United States Patent
Scheuering

(10) Patent No.: US 6,934,362 B2
(45) Date of Patent: Aug. 23, 2005

(54) X-RAY SYSTEM AND METHOD TO DETERMINE THE EFFECTIVE SKIN INPUT DOSE IN X-RAY EXAMINATIONS

(75) Inventor: Peter Scheuering, Fürth (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 10/846,250

(22) Filed: May 14, 2004

(65) Prior Publication Data

US 2005/0002489 A1 Jan. 6, 2005

(30) Foreign Application Priority Data

May 16, 2003 (DE) .......................................... 103 22 143

(51) Int. Cl.$^7$ .............................................. H05G 1/44
(52) U.S. Cl. ...................................... 378/108; 378/207
(58) Field of Search ............................. 378/64, 65, 97, 378/108, 117, 207

(56) References Cited

U.S. PATENT DOCUMENTS 6,330,299 B1 * 12/2001 Curtis et al. .................. 378/62
6,422,751 B1 * 7/2002 Aufrichtig et al. .......... 378/207

FOREIGN PATENT DOCUMENTS

| DE | PS 38 10 501 | 2/1996 |
| DE | OS 197 30 519 | 1/1999 |

* cited by examiner

Primary Examiner—Edward J. Glick
Assistant Examiner—Courtney Thomas
(74) Attorney, Agent, or Firm—Schiff Hardin LLP

(57) ABSTRACT

In an X-ray system and method to determine the effective skin input dose in x-ray examinations, the skin input dose is obtained by dividing the measured dose area product by the exposed skin input area, which is calculated from the exposed area in the film or image intensifier plane, geometric data of the x-ray system, and the thickness of the body part of the patient to be examined. The water equivalent determined from the setting values for the irradiation is used as the value for the thickness of the body part to be examined.

9 Claims, 1 Drawing Sheet

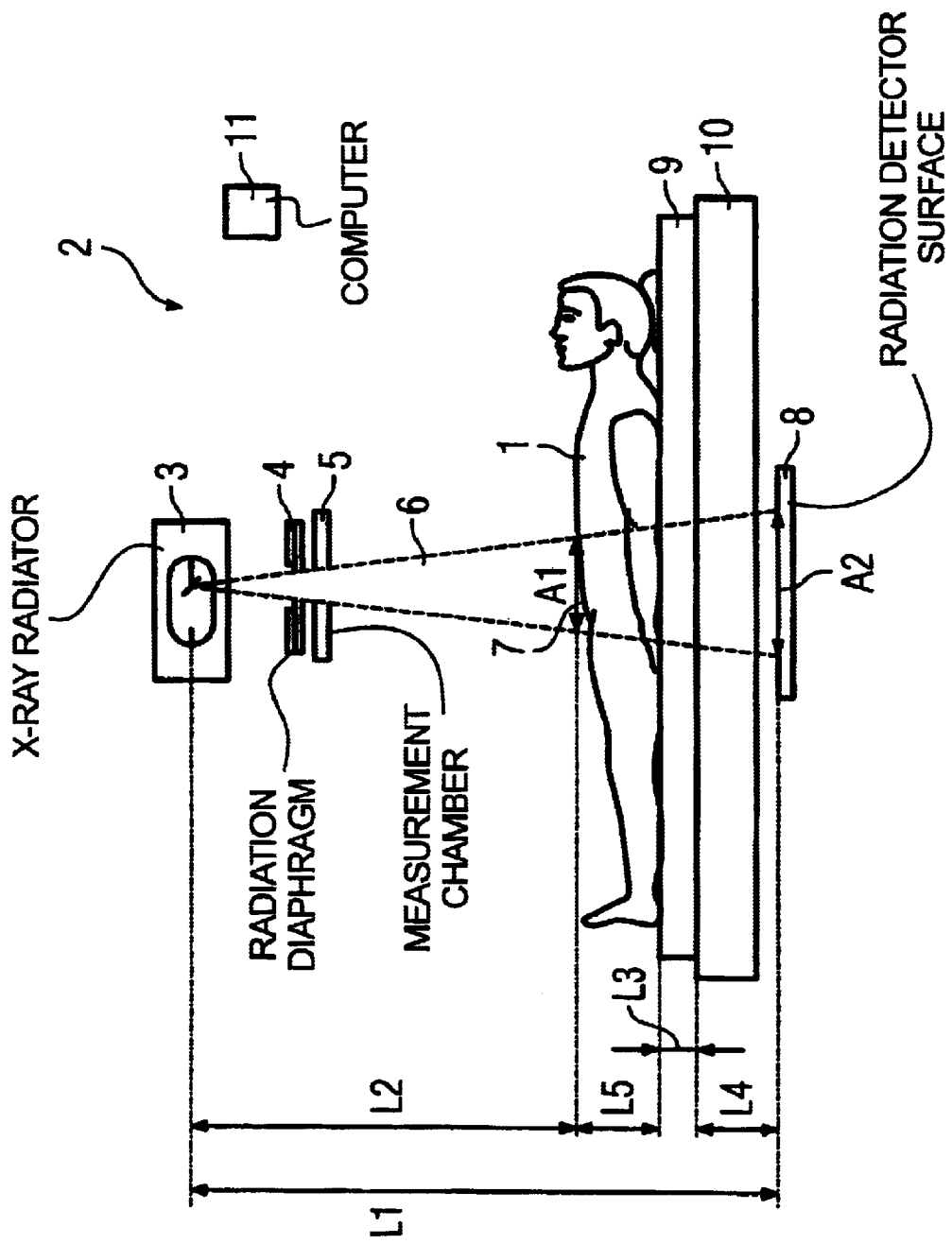

X-RAY SYSTEM AND METHOD TO DETERMINE THE EFFECTIVE SKIN INPUT DOSE IN X-RAY EXAMINATIONS

BACKGROUND OF THE INVENTION

1. Field of the Invention

The present invention concerns a method and x-ray apparatus to determine the effective skin input dose in x-ray examinations. In particular, it concerns a method and apparatus of the type wherein the skin input dose is obtained by dividing the measured dose area product by the exposed skin input area, which is calculated from the exposed area in the film plane or image intensifier input screen plane, geometric data of the x-ray system, and the thickness of the body part of the patient to be examined.

2. Description of the Prior Art

Conventional x-ray systems possess a dose area measurement device that generally is disposed beneath the radiation diaphragm in the beam path. This measurement device has a measurement chamber and supplies the dose area product, which is also abbreviated as a dose area. More important than the dose area product, however, is the effective operative dose to which the patient is exposed in the x-ray examination. This effective operative dose or skin input dose is calculated from the dose area product divided by the effective exposed skin input area. The skin input area is different from patient to patient; it depends in particular on the thickness of the body part of the patient to be examined, since the distance of the focus from the skin surface is different in each patient. The diameter or the thickness of the body part to be examined can fluctuate dependent on the body position and build, for example between 0 cm and 50 cm. Because of such variations, in many cases only the dose area product is registered, but this is not very significant.

It is also possible to measure the distance of the radiation source to the patient manually with a measuring tape; but this procedure is very difficult and not particularly precise.

To determine and adjust a desired radiation dose in x-ray apparatuses, it is specified in German OS 197 30 519 to firmly mount a dosimeter in the beam path of the x-ray tube to measure the radiation dose emitted by the x-ray tube. Thus the radiation dose thus is determined and not the skin input dose.

German Patent 38 10 501 C2 discloses an x-ray measurement apparatus with two radiation detectors disposed in the primary beam cone, between which lies a region of an examination subject. From output signals of these detectors a signal corresponding to the patient transparency is formed. A range finder for the focus-patient distance (FOBJ) is present, and the incident dose power given irradiation, exposure without a patient, as well as the patient transparency given exposure, are determined from the output signals of the radiation detectors and the range finder. Again, the skin input dose is not determined here.

SUMMARY OF THE INVENTION

An object of the present invention is to provide a method and x-ray apparatus to determine the effective skin input dose in x-ray examinations, which can be implemented more simply.

This object is achieved in accordance with the present invention by a method and apparatus of the type initially described wherein the water equivalent determined from the setting values for the irradiation is used as the value for the thickness of the body part to be examined.

The water equivalent, also known as the water equivalent value or the water phantom thickness, is based (as described, for example, in "Radiation Dosimetry for Extremity Radiographs" by Huda and Gkanatsios, Health Physics, page 492 to 499, 1998) on the assumption that water and body tissue behave essentially the same with regard to attenuation of x-ray radiation. Thus 1 cm water corresponds to approximately 1 cm body tissue. The water equivalent is determined during the irradiation and serves to determine an optimal kV value for the x-ray exposure.

The water equivalent can be calculated from the apparatus parameters used in the irradiation. These setting values are known after each irradiation, so the water equivalent can be determined simply. The water equivalent generally coincides up to a few percentage points with the actual thickness of the body part of the patient to be examined. The focus-patient distance, which conventionally could only be determined manually by direct measurement of the distance, can be automatically calculated with the known thickness or the diameter of the examined body part.

In the inventive method, the water equivalent can be determined from the x-ray voltage and/or the x-ray current and/or the grid attenuation and/or the filter attenuation and/or the film-focus distance and/or a normalization factor. In this manner, all parameters are considered that can have an influence on the water equivalent. (The film-focus distance is a term of art meaning the distance between the focus of the x-ray source and the detector surface of the radiation detector, even if the radiation detector does not happen to involve film.)

In the inventive method, the exposed skin input area is calculated from the exposed area in the film plane or image intensifier plane (radiation detector plane), the film-focus distance and the focus-patient distance. The focus-patient distance is first calculated from the water equivalent. The film-focus distance can in fact be variable, since the radiation is adjustable in terms of height; however, the distance between the radiator and the film is a known quantity. The exposed area in the film plane or image intensifier plane is likewise known, such that the effective exposed skin input area, which is different for each patient, can be calculated from such data.

The focus-patient distance is calculated from the film-focus distance, the thickness of the patient support, the distance between the topside of the table top, and the film or image intensifier input and the thickness of the body part of the patient to be examined. The thickness of the tabletop or the distance of the upper edge of the table top from the film or from the image intensifier input screen is known and is normally a constant quantity. The thickness of the patient support is likewise known for the particular apparatus. The sought focus-patient distance can be determined together with the thickness of the body part to be examined (determined from the water equivalent) and the film-focus distance. The effective exposed skin input area can be subsequently calculated from this with the beam settings, if the dose area product is divided by the effective exposed skin input area, the sought effective operative dose is obtained.

The inventive method is particularly user-friendly when the skin input dose is automatically determined by a computer device. In an embodiment of the invention the determined skin input dose is displayed on the x-ray apparatus after the irradiation.

As noted above, the invention also concerns an x-ray apparatus with a measurement means for the dose area product arranged in the beam path.

The inventive x-ray system has a computer device to determine the effective skin input dose, the skin input dose being determined from the measured dose area product and the calculated exposed skin input area.

The inventive x-ray system is fashioned such that the effective exposed skin input dose is determined by the computer device using the exposed area in the film plane or image intensifier plane, geometric data of the x-ray system, and the thickness of the body part of the patient to be examined.

So that the skin input dose can be automatically determined, the computer device of the inventive x-ray system is fashioned such that the water equivalent determined from the parameters for the irradiation is used as the value for the thickness of the body part of a patient to be examined.

DESCRIPTION OF THE DRAWING

The single FIGURE is a schematic illustration of an x-ray system constructed and operating in accordance with the principles of the present invention.

DESCRIPTION OF THE PREFERRED EMBODIMENTS

The single FIGURE schematically shows, in a side view, a patient 1 in an x-ray system 2 during an x-ray examination.

The x-ray system 2 has a radiator 3 that emits x-rays 6 that are incident on a diaphragm 4, and a measurement chamber 5 disposed below a radiation diaphragm 4.

The x-ray field 6 is incident on the exposed skin input area A1 of the surface 7 of the patient 1. The x-rays penetrate the patient 1 and strike the detector surface 8 of an x-ray film or an image intensifier input screen. In the FIGURE, the area A2 of the detector surface 8 irradiated by the x-ray field 6 is also shown. A solid-state detector also can be used.

The measurement chamber 5 supplies the dose area product after the implementation of the x-ray acquisition. It is the effective operative dose that is sought, and thus the dose area product must be divided by the effective exposes skin input area A1. This skin input area A1 is, however, initially unknown, since it depends on the thickness or height of the surface 7 of the body part of the patient 1 to be examined.

All technical parameters of the x-ray exposure are known, however, which include the x-ray voltage, the x-ray current, the raster damping, the filter damping, the film-focus distance and a normalization factor. The water equivalent can be determined from these values, and this calculation can be implemented automatically by the x-ray system in a computer device 11. This water equivalent indicates about the properties of the examined body in the x-ray exposure in comparison with water. The water equivalent has the dimension of length and is a very good approximate value for the thickness of the examined body part. The water value accordingly corresponds in the shown exemplary embodiment to the value L5, which specifies the patient thickness. Further known geometric parameters are the thickness of the patient support L3 (which can be, for example, a pad 9), as well as the distance L4 between the detector surface 8 and the upper edge of a tabletop 10. The radiation 3 is height-adjustable, but the film-focus distance L1 is always known. With these known geometric data L1, L3, L4 and L5, the sought distance L2 between the focus or radiator 3 and the patient 1 can be calculated with the formula:

$$L2 = L1 - L3 - L4 - L5$$

The formula for the calculation of the skin input area A1 results from the beam settings:

$$A1 = A2 \cdot (L2/L1)^2$$

The area A2 designates the exposed area portion of the detector surface 8. The sought effective operative dose D can be calculated with this known skin input area A1:

$$D = \text{dose area product}/A1$$

The determination of the effective dose D can be implemented in the computer 11, which is schematically shown in the FIGURE. The computer 11 is connected with the system components of the x-ray system 2 via connection lines (not shown), such that it can access all relevant geometric and irradiation data. The computer 11 also can have a display or be connected with an external display, such that the measurement or calculation results are directly displayed to the user.

The opening of the diaphragm 4 is not necessarily quadratic; it can also be rectangular. In this case, the area A2 is calculated from the diaphragm width times the diaphragm height.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for determining an effective skin input dose in an x-ray examination conducted with an x-ray system having an x-ray source that emits x-rays that are incident on a detector surface of a radiation detector, said x-ray system having geometric data associated therewith, comprising the steps of:

measuring a dose area product of said x-rays;

calculating an exposed skin input area of an examination subject to be irradiated with said x-rays from an exposed area of said detector surface exposed by said x-rays, said geometric data, and a thickness of a body part of the subject;

determining a water equivalent from setting values for operating said x-ray source and using said water equivalent as a value for said thickness; and dividing said measured dose area product by said exposed skin input area to obtain said effective skin input dose.

2. A method as claimed in claim 1 wherein said x-ray source is operated with an x-ray voltage and an x-ray current, and has a grid exhibiting a grid attenuation for said x-rays and a filter exhibiting a filter attenuation for said x-rays, and wherein said x-ray source has a focus from which said x-rays originate, said focus being disposed at a distance from said detector surface, and wherein said setting values comprise at least one of said x-ray voltage, said x-ray current, said grid attenuation, said filter attenuation, said distance, and a normalization factor.

3. A method as claimed in claim 1 wherein said x-ray source has a focus from which said x-rays emanate, and wherein said geometric data include a distance betweens aid focus and said detector plane, and comprising calculating said exposed skin input area from said exposed area on said detector surface, said distance between said focus and said detector surface, and a distance between said focus and the subject.

4. A method as claimed in claim 3 wherein said x-ray system has a patient table having a tabletop with a top side, a patient support disposed on said topside of said tabletop having a thickness and adapted to receive the subject thereon, and comprising calculating the distance between the focus and the subject from said distance between the focus and the detector surface, said thickness of said patient support, a distance between said topside of said tabletop and said detector surface, and said thickness of the body part of the subject to be examined.

5. A method as claimed in claim 1 comprising automatically calculating said skin input dose electronically in a computer.

6. A method as claimed in claim 1 comprising displaying said skin input dose at said x-ray system after irradiating the subject.

7. An x-ray system comprising;

an x-ray source for emitting x-rays from a focus;

a radiation detector having a detector surface on which said x-rays are incident, said x-ray source and said radiation detector being adapted to receive a patient therebetween;

a measurement arrangement for measuring a dose area product of said x-rays; and a computer for automatically electronically calculating an exposed skin input area of the patient irradiated with said x-rays, and for automatically electronically calculating an effective skin input dose of said x-rays for the patient using the measured dose area product and the calculated exposed skin input area.

8. An x-ray system as claimed in claim 7 having geometric data associated therewith, and wherein said computer determines said effective skin input dose from an exposed area on said detector surface irradiated by said x-rays, said geometric data, and a thickness of a body part of the patient to be irradiated.

9. An x-ray system as claimed in claim 8 wherein said x-ray source is operated with operating parameters for generating said x-rays, and wherein said computer determines a water equivalent from said operating parameters and uses said water equivalent as a value for said thickness.

\* \* \* \* \*